(12) United States Patent
Berk et al.

(10) Patent No.: US 8,535,058 B1
(45) Date of Patent: Sep. 17, 2013

(54) DENTAL RELEASE AGENT AND METHODS FOR ITS USE

(75) Inventors: Kenneth J. Berk, Newton, MA (US); Anthony R. Silvestri, Jr., Plymouth, MA (US)

(73) Assignee: Pulpdent Corporation, Watertown, MA (US)

( * ) Notice: Subject to any disclaimer, the term of this patent is extended or adjusted under 35 U.S.C. 154(b) by 542 days.

(21) Appl. No.: 12/695,499

(22) Filed: Jan. 28, 2010

(51) Int. Cl.
 A61C 17/00 (2006.01)
 A61C 9/00 (2006.01)
 A61C 5/00 (2006.01)

(52) U.S. Cl.
 USPC .......................................... 433/214; 433/217.1

(58) Field of Classification Search
 USPC ................ 433/37–48, 213, 214, 217.1, 215, 433/229, 226; 264/16–20, 213, 300; 523/101, 523/107, 109, 120; 424/49, 58, 401; 406/548, 406/609; 427/2.1, 2.24, 2.29; 426/548, 609
 See application file for complete search history.

(56) References Cited

U.S. PATENT DOCUMENTS

| | | | | |
|---|---|---|---|---|
| 1,431,425 A | * | 10/1922 | Richmond | 433/222.1 |
| 2,197,719 A | * | 4/1940 | Conner | 426/4 |
| 3,561,119 A | * | 2/1971 | Susman et al. | 433/213 |
| 3,661,605 A | * | 5/1972 | Rubin et al. | 106/244 |
| 3,974,293 A | * | 8/1976 | Witzel | 426/4 |
| 4,881,898 A | * | 11/1989 | Harvey et al. | 433/215 |
| 4,975,059 A | * | 12/1990 | Sendax | 433/173 |
| 5,104,317 A | * | 4/1992 | Riazi | 433/136 |
| 5,503,866 A | * | 4/1996 | Wilhelm, Jr. | 426/609 |
| 5,824,359 A | | 10/1998 | Khan et al. | |
| 5,888,480 A | | 3/1999 | Homola et al. | |
| 5,911,580 A | * | 6/1999 | Sharp et al. | 433/213 |
| 6,623,780 B1 | | 9/2003 | Stevens et al. | |
| 6,881,449 B2 | | 4/2005 | Augello et al. | |
| 2007/0275132 A1 | | 11/2007 | Paul et al. | |
| 2008/0160136 A1 | * | 7/2008 | Gebhardt et al. | 426/72 |
| 2009/0075235 A1 | * | 3/2009 | Letcher | 433/173 |

FOREIGN PATENT DOCUMENTS

| EP | 0180483 | * | 5/1986 |
|---|---|---|---|
| WO | WO-2005096835 A1 | | 10/2005 |
| WO | WO-2008057693 A2 | | 5/2008 |

* cited by examiner

*Primary Examiner* — Todd Manahan
*Assistant Examiner* — Michael R Ballinger
(74) *Attorney, Agent, or Firm* — Cesari and McKenna, LLP

(57) ABSTRACT

An oil-free aqueous lecithin composition is suitable as a release agent and lubricant for dental procedures. Layered between a first entity and a second entity during a dental procedure, the composition promotes ready separation of the first entity from the second entity as needed in the procedure.

26 Claims, 2 Drawing Sheets

DENTAL RELEASE AGENT AND METHODS FOR ITS USE

BACKGROUND OF THE INVENTION

1. Field of the Invention

This invention relates to lubricants and release agents for dental procedures. In particular, a lubricant, separating agent, and dental release agent composition and methods for its use are described.

2. Background Information

Dental procedures commonly entail temporarily holding a dental material in contact with teeth or other anatomical structures in the mouth. When the dental material has served its therapeutic or diagnostic function, it is removed from the mouth. A common problem in using such temporarily placed dental materials is sticking between the oral structures and the dental material which can ruin the procedure or make removal of the material difficult.

The case of dental impressions is instructive. A dental impression is an imprint, formed in a compliant material, of teeth, gums and other structures of interest in the mouth. The imprint preserves a "negative" from which a model of the structures may be constructed.

A dental impression is conventionally taken by holding a mass of polymerizable semi-liquid impression material around the structures of interest until the material sets into a flexible solid. Known impression materials include sodium alginate, polyether, polyvinyl siloxane, and other silicones. When the set impression material is removed from the mouth, it retains the negative imprint of the spatial features of the structures of interest. Thus dental impressions may be a diagnostic tool or serve as an intermediate article in fabricating, for example, orthodontic appliances, dentures, crowns, and other prostheses.

Because of sticking between the set impression material and the surfaces of teeth and mucosa, removing the set impression from the mouth can require a degree of force uncomfortable to the patient. Also, detachment may require torque sufficient to permanently distort the impression, resulting in an inaccurate model and, consequently, an ill-fitting restoration or appliance. Furthermore, it is not unusual for impression material to be inadvertently deposited on tissue outside the mouth such as lips, skin, or hair. Removing this adherent extraneous material can be difficult and is a nuisance to the patient.

Because of the difficulties illustrated by this instructive example, a compatible release agent would be advantageous. The use of petroleum jelly as this release agent is commonplace in many dental procedures. However, the properties of petroleum jelly render it unsatisfactory for many dental uses. Petroleum jelly is not water based and not easily removed by water. Its greasy residue remaining after washing may be displeasing to the patient and may also interfere with subsequent intra-oral procedures. Petroleum jelly is thick and difficult to spread evenly. The resulting local variations in coating thickness may adversely affect the accuracy of the dental procedure. Also, the prevalent is mode of dispensing petroleum jelly, dipping into a jar, lends itself to cross-contamination between patients.

Another type of dental material prone to sticking to teeth is a dental dam. Cling between the teeth and the dam may make placement difficult and result in tearing of the dam. However, petroleum jelly is incompatible with latex. The prevalent alternative lubricant is greaseless shaving cream, the flavor and consistency of which is suboptimal for intra-oral use.

There is a need, therefore, for a lubricant and release agent compatible with dental procedures.

SUMMARY OF THE INVENTION

An oil-free dispersion of lecithin in water is a release agent and lubricant for dental procedures. The lecithin may constitute at least 10% by weight of the composition. In use, a layer of the composition is placed in the mouth as a barrier between a first entity and a second entity. The barrier promotes ready separation of the first entity from the second entity as needed in a dental procedure.

BRIEF DESCRIPTION OF THE DRAWINGS

The invention description below refers to the accompanying drawings, wherein identical reference symbols designate like structural or functional elements, and in which.

Figure 1:
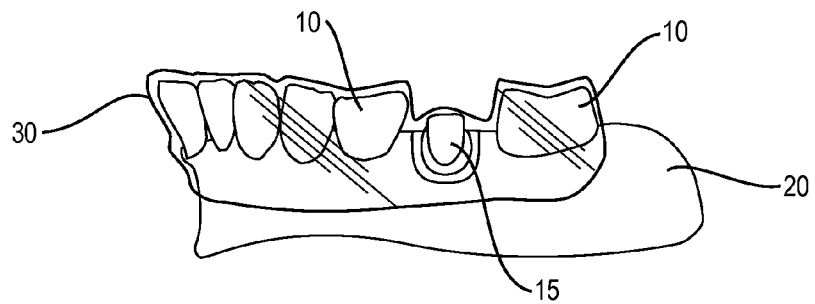
FIG. 1 is a side elevational view of bottom teeth and gums coated with the aqueous lecithin dental release agent according to the invention.

Features in the figures are not, in general, drawn to scale.

DETAILED DESCRIPTION OF ILLUSTRATIVE EMBODIMENTS

The oil-free aqueous lecithin composition incorporates lecithin constituting at least 10%, 15%, or 20% or more of the total weight of the composition. Or, the amount of lecithin present in the composition may be equal to one fifth or more of the amount of water present, by weight. As used herein, "lecithin" encompasses a complex mixture of phosphatides, as is known to those skilled in the art, and not only pure phosphatidyl choline. The lecithin may be derived from soybeans. Illustratively, the lecithin is deoiled and comprises 0 to 5% oil by weight. In one embodiment, the lecithin is Solec™ 8120, a hydroxylated soy lecithin used in food products (Solae Company®, St Louis). As used herein, "oil-free" means that the composition is no more than 0.5% oil not including any oil comprised by or contained in the lecithin. Such incidental traces of oil may be introduced by, e.g., a surfactant or flavoring ingredient as described below.

The composition may incorporate additives to enhance its features for use as a release agent or lubricant in dental applications. For example, an additional surfactant, for example a silicone surfactant of the Silwet series (Momentive Performance Materials, Wilton, Conn.), may promote spreading of the composition on anatomical structures or dental materials. A sweetener and/or other flavorings may be added to render the composition more palatable or otherwise aesthetically appealing to patients. Antimicrobial agents such as bacteria or mold inhibitors or other preservatives maintain shelf life. Maintaining the pH of the composition between 4 and 6 also discourages microbe growth. We have found that, apart from sweetening properties, the presence of a sugar alcohol such as xylitol in the composition imparts improved handling and spreading and therefore results in a more efficacious lubricant and release agent. Other sugar alcohols include mannitol, sorbitol, erythritol, maltitol, lactitol.

An illustrative embodiment of an aqueous lecithin composition suitable for use as a dental release agent and lubricant was produced using the ingredients and amounts listed in Table 1. The distilled water at room temperature was placed in a plastic container to which the potassium sorbate, sodium benzoate and xylitol was then added. At this point, processing of the container contents using a Dispersator (Premier Mill) was begun. Continuous mixing by the Dispersator was maintained throughout the addition of the remaining ingredients to the container. When the sorbate, benzoate and xylitol had completely dissolved in the water, the malic acid was added to the solution. When the acid had completely dissolved, the lecithin powder was slowly added to the vortex while maintaining Dispersator speed. From the time that the lecithin was fully incorporated, the contents of the container were processed for about twenty minutes with occasional changes in the blade position. At the end of the twenty minutes the silicone surfactant and fragrant maskant were mixed into the container. The composition was processed for an additional four to five minutes.

TABLE 1

|  | Function | Wt % |
| --- | --- | --- |
| Distilled water |  | 71.25 |
| Solec ™ 8120 hydroxylated deoiled soy lecithin |  | 21.46 |
| Potassium sorbate | Preservative | 0.10 |
| Sodium benzoate | Preservative | 0.10 |
| Xylitol | Flavor, Viscosity adjustment | 6.00 |
| DL-malic acid | pH adjustment | 0.52 |
| Silicone surfactant | Surfactant | 0.12 |
| Lemon fragrant maskant | Flavor | 0.18 |

The composition was let stand for at least about 24 hours to allow the release of incorporated air before transferring to an air-tight package. Alternately, the contents of the container could have been subjected to vacuum during the final minutes of processing. Illustratively the package allows the dispensing of small volumes of the composition without introducing air into the portion remaining in the package. In one approach, the package is constructed so that expressing a volume of the composition causes the bottom of the cavity to rise so that no air is drawn through the composition. Stored in such packaging, the illustrative composition may have a shelf life on the order of one to two years or longer and lends itself to single-use dispensing without risking contamination of the unused portion.

The aqueous lecithin composition is particularly useful as a dental lubricant or release agent. The composition is a water-soluble liquid, nongreasy and easy to remove after use. After application, for example by swabbing with a cotton pellet, the composition may be easily spread by compressed air to cover structures of interest with a uniform, very thin yet very effective layer. Typically, about 0.5 ml of the composition is adequate to cover a bottom or top set of teeth. The inert nature of the composition and its compatibility with latex renders it usable in a wide range of dental procedures.

In use, a quantity of the aqueous lecithin dental release agent is placed in, on or near the mouth as an ancillary to a dental procedure. The aqueous lecithin dental release agent is situated to form a barrier between distinct entities, i.e., materials, tissues, or objects, brought into contact in the course of the dental procedure. The aqueous lecithin dental release agent allows the entities to be readily separated at the end of the dental procedure. Thus the composition may support dental procedures which involve, e.g., situating a rubber dam, taking dental impressions, relining dentures, trying in an implant abutment, fitting a temporary restoration, removing stray impression material or cement, and protecting tissue outside the mouth.

In one approach, the first entity is a substrate in the mouth. The second entity, designated a treatment material, is applied temporarily over the substrate and then removed from the substrate and the mouth. In this approach, the aqueous lecithin dental release agent is first applied directly onto all or part of the intra-oral substrate. The treatment material is then applied over the separating medium on the substrate. After a treatment interval, when the applied treatment material has served the desired purpose, the applied treatment material is removed from the substrate whereas the substrate remains in place in the mouth.

The presence of the aqueous lecithin dental release material between the substrate and the treatment material inhibits sticking or adhesion between them and allows ready separation of the two entities. In the method, the aqueous lecithin dental release agent may be furthermore applied to facial hair and to the lips and skin around the mouth to facilitate removal of stray treatment material from tissue near the mouth.

In one embodiment, the procedure produces a conventional impression, from which a representation of dentition can be made. With reference to FIG. 1, the intra-oral structures of interest constituting the substrate in an illustrative impression procedure include teeth 10 and a preparation 15 projecting from gums 20. The preparation 15 is a portion of a tooth prepared to be fit with a restoration, as is known to those skilled in the art. The aqueous lecithin dental release agent is applied to form a thin coating 30 of the release agent over the teeth 10, preparation 15 and/or gums 20. For clarity of demonstration of the illustrative method, the coating 30 is drawn relatively thick in the figures. The conformal coating 30 of the aqueous lecithin dental release agent is in fact illustratively a thin layer imperceptible to the eye. The coating 30 of the release agent may be created by, for example, painting the medium onto the facial and labial (not shown) dental and gingival surfaces. Further spreading and thinning of the coating 30 of the release agent over the structures 10, 15 and 20 to promote uniform coverage and thickness may be effected by directing compressed air at the coating 30.

Figure 2:
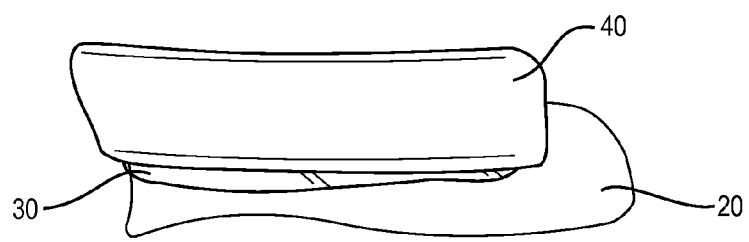
FIG. 2 is a side elevational view of the bottom teeth and gum with impression material over the release agent.
Figure 3:
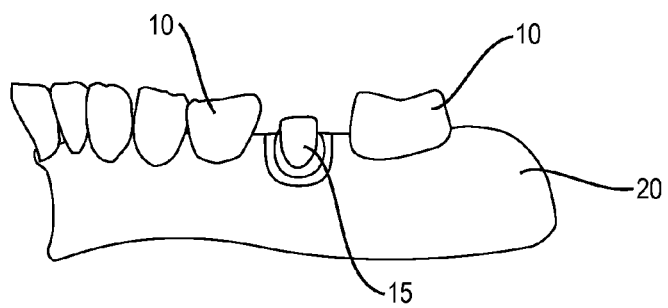
FIG. 3 is a side elevational view of bottom teeth and gums after removal of the impression material and release agent.

The impression material is prepared and, conventionally, placed in a tray in which the material is conveyed into the mouth, as is known to those skilled in the art. The impression material 40 is applied to the teeth 10 and gums 20, over the coating 30, as shown in FIG. 2, and held in place by the tray (not shown). When the material 40 has set sufficiently to retain the features of the substrate the material 40 is removed from the mouth. After removal of the material 40, residue of the film 30 of aqueous lecithin dental release agent may be readily removed, as shown in FIG. 3, by wiping and/or water spray.

The presence of the coating 30 of aqueous lecithin dental release agent between the impression material 40 and the substrate, as shown in FIG. 2, reduces sticking of the material 40 in the mouth. Easy release of the set impression may enhance patient comfort and prevent distortion due to torque and other stresses during removal from the mouth. The low viscosity of the aqueous lecithin dental release agent may impart sufficient thinness and spreadability to the coating 30 to allow the formation of an accurate impression. The coating 30 illustratively stays in place as long as needed but is easily removed after the procedure.

The set impression may be suitable for use in fabricating a restoration to be fit onto the preparation 15. If the impression is to be used in fabricating a permanent restoration, the coating 30 of the aqueous lecithin dental release agent has appropriate viscosity so that it may be applied to the teeth 10 while leaving the preparation 15, the adjacent part of the gums 20 and any other potentially critical areas uncoated to avoid compromising the accuracy of the fit between the fabricated permanent restoration and the preparation 15.

In an alternative embodiment, the substrate may be a preparation or build up ready to be outfitted for a temporary restoration serving as the treatment material, as is known to those skilled in the art. The aqueous lecithin dental release agent is applied to the substrate and adjacent tissues before the temporary restoration is placed thereon. Once set, the temporary restoration can be easily removed. The aqueous lecithin dental release agent applies evenly and in such thin layers that the temporary restoration to may remain in place up to several months, with temporary cement, yet be easily removed at the end of the treatment interval.

In another alternative embodiment, the treatment material may be dental cement. The aqueous lecithin dental release agent is first applied to mucosa and one or more teeth not intended to bond with the cement. Coating the surface to be bonded is avoided. After cement has been applied to the intended bonding surface in the mouth, any cement adventitiously contacting the nonbonding surface of the substrate is easily removed.

In another approach, the first entity is an element to be deployed in the mouth. A coating of the aqueous lecithin dental release agent is first applied to the element. As understood herein, a coating does not necessarily cover the entire exterior of the element. The release agent inhibits adhesion between the element and a second entity that the element may contact in the mouth, either adventitiously or by design. The aqueous lecithin dental release agent thereby allows facile separation of the first and second entities.

Figure 4:
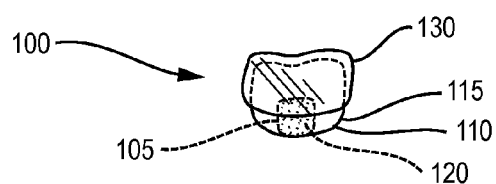
FIG. 4 shows a crown containing cement on its interior and coated on its exterior with aqueous lecithin dental release agent according to the invention.

In an illustrative procedure, the element may be a restoration to be cemented into the mouth. With reference to FIG. 4, a crown 100 is constructed with a cavity 105, an exterior surface 115 and a lower bonding surface 110. The cavity 105 contains cement 120. A coating 30 of the aqueous lecithin dental release agent is applied to the exterior surface 115 of the crown 100. A border free of the release agent may be maintained near the lower bonding surface 110 to avoid compromising the expected bonding of the crown 100 in the mouth.

Figure 5:
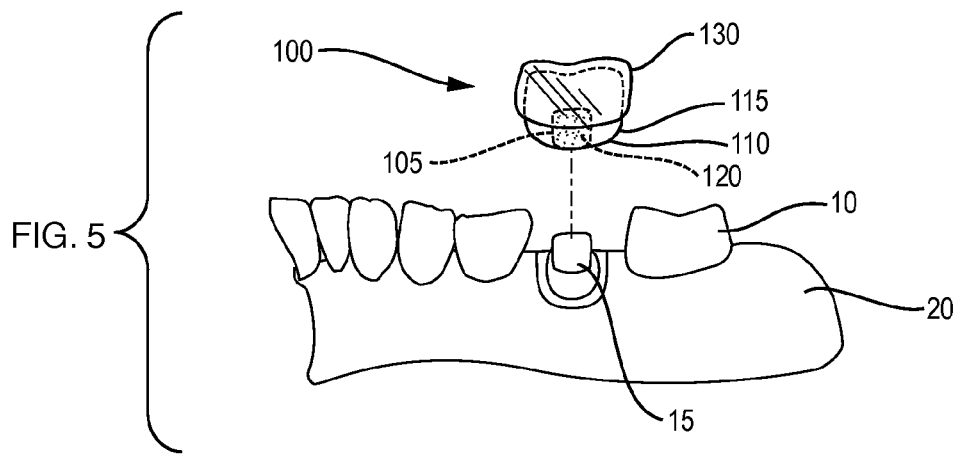
FIG. 5 shows the crown over a corresponding preparation.
Figure 6:
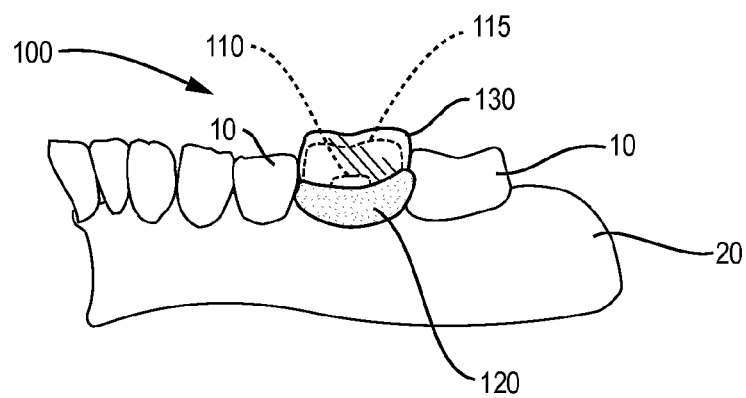
FIG. 6 shows extruded cement as the crown is luted to the preparation.
Figure 7:
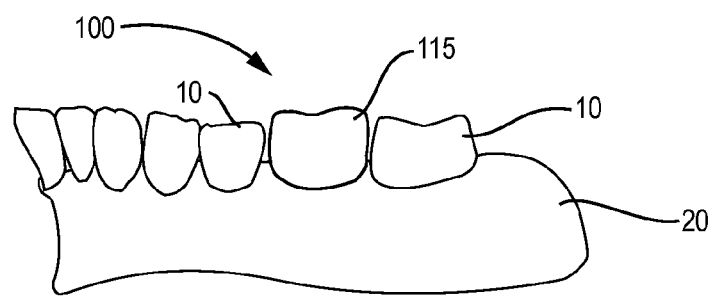
FIG. 7 shows the crown in place after cement removal.

With reference to FIG. 5, the cavity 120 complements the preparation 15. As the cavity 120 and preparation 15 are mated, cement 120 is extruded from the cavity 105 over the coating 30 on the exterior surface 115, as shown in FIG. 6. The cement 120 may be removed from the exterior surface 115 of the crown 100 easily due to the barrier constituted by the coating 30 of aqueous lecithin dental release agent. FIG. 7 shows the exterior surface 115 of the crown 100 free of cement 120 at the end of the procedure.

In an alternative embodiment, the element may be an implant abutment constructed to fit onto a dental implant, constituting the second entity, situated in the jaw. The surfaces on the implant to be contacted by the abutment constitute an intra-oral surface. The abutment is conventionally placed on the implant in the mouth temporarily in a try-in procedure before final installation, as known to those skilled in the art. In general, the fit between the abutment, illustratively of a ceramic material, and the implant, illustratively of metal, is fabricated very precisely and movement of the abutment on the implant is consequently difficult. In the embodiment, a coating of the aqueous lecithin dental release agent is applied to the surface of the abutment before its placement onto the implant in the mouth during the try-in procedure. The aqueous lecithin dental release agent lubricates the contact between the abutment and the implant during try-in, facilitating movement of the abutment during installation and removal.

In another alternative embodiment, the element is the buccal surfaces of a denture and the second entity is an impression material. During a reline procedure, impression material is placed in the denture base and the base placed in the mouth as if being worn by the patient, as known to those skilled in the art. In the embodiment, a coating of the aqueous lecithin dental release material is first applied to the buccal surfaces of the denture. After removal of the denture and impression material from the mouth, the presence of the release material allows the easy removal of extraneous impression material from the buccal surfaces of the denture.

In yet another alternative embodiment, the first entity is a dental dam. The illustrative dental release agent is applied to the surface of the dam intended for contact with intra-oral structures. The release agent imparts sufficient slip between the substrate and the dam to allow placement of the dam in the desired position without tearing.

Although specific features are included in some embodiments and not in others, it should be noted that individual feature may be combinable with any or all of the other features in accordance with the invention. Furthermore, other embodiments may be compatible with the described features.

It will therefore be seen that the foregoing represents a highly advantageous approach to procedures involving temporary contact between a first entity and a second entity, particularly for dental applications. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of treating an oral substrate, comprising:
   applying to the oral substrate a composition containing lecithin and water, wherein the lecithin constitutes at least 10% by weight of the composition and wherein the oral substrate is at least one of a tooth, a mucosa, a gum, a dental implant, a denture, a restoration, a lip, and skin around the mouth;
   applying a material over the composition; and
   removing the material from the oral substrate.

2. The method of claim 1 wherein the lecithin is 0% to 5% oil by weight.

3. The method of claim 1 wherein the lecithin is hydroxylated.

4. The method of claim 1 wherein the lecithin constitutes at least 15% of the total weight.

5. The method of claim 1 wherein the lecithin and the water are present in a ratio of at least 1 to 5.

6. The method of claim 1 wherein applying and removing the material forms an impression of teeth.

7. The method of claim 1 wherein the composition further comprises a sweetener.

8. The method of claim 1 wherein the composition further comprises a preservative.

9. The method of claim 7 wherein the composition further comprises a preservative and a surfactant.

10. The method of claim 1 wherein the oral substrate comprises a dental surface.

11. The method of claim 1 wherein the material comprises a temporary restoration.

12. The method of claim 1 wherein the material comprises cement.

13. The method of claim 1 further comprising separating the material from the oral substrate using the composition.

14. A method comprising:
coating a dental element with a composition containing lecithin and water, the lecithin constituting at least 10% by weight of the composition; and
placing the coated dental element in a mouth.

15. The method of claim 14 wherein the dental element is a restoration.

16. The method of claim 14 wherein the composition coated on the dental element is placed in contact with an intra-oral surface and further comprising removing the element from the mouth.

17. The method of claim 16 wherein the dental element is a rubber dam.

18. The method of claim 16 wherein the dental element is an implant abutment.

19. The method of claim 14 further comprising removing a stray substance from the composition coated on the dental element in the mouth.

20. The method of claim 14 wherein the lecithin is hydroxylated and 0% to 5% oil by weight, and the composition further comprises a preservative and a sweetener.

21. A method of treating a mouth, comprising:
providing a composition having a total weight containing hydroxylated soy lecithin, water, xylitol, and a preservative, wherein the hydroxylated soy lecithin constitutes at least 10% of the total weight of the composition and wherein the lecithin is 0% to 5% oil by weight and no more than 0.5% oil, not including the 0% to 5% oil by weight of the lecithin;
placing the composition in the mouth between and in contact with a first entity and a second entity; and
separating the second entity from the first entity.

22. The method of claim 21 wherein the second entity is cement.

23. The method of claim 21 wherein the second entity is impression material.

24. The method of claim 21 wherein the second entity is a dental dam.

25. The method of claim 21 further comprising
applying the composition onto tissue around the mouth;
placing material over the tissue; and
removing the material from the tissue.

26. The method of claim 21 wherein the second entity is separated from the first entity by removing the second entity from the mouth while the first entity remains in the mouth.

* * * * *